(12) United States Patent
Lee (10) Patent No.: US 10,441,489 B2
(45) Date of Patent: Oct. 15, 2019

(54) EXCRETA DISPOSAL APPARATUS COMPRISING MALE MODULE

(71) Applicant: CURACO, INC., Seongnam-si, Gyeonggi-do (KR)

(72) Inventor: Hoonsang Lee, Seoul (KR)

(73) Assignee: Curaco, Inc., Seongnam-Si, Gyeonggi-Do (KR)

( * ) Notice: Subject to any disclaimer, the term of this patent is extended or adjusted under 35 U.S.C. 154(b) by 0 days.

(21) Appl. No.: 15/548,230

(22) PCT Filed: Feb. 3, 2015

(86) PCT No.: PCT/KR2015/001117
§ 371 (c)(1),
(2) Date: Aug. 2, 2017

(87) PCT Pub. No.: WO2016/125928
PCT Pub. Date: Aug. 11, 2016

(65) Prior Publication Data
US 2018/0028386 A1 Feb. 1, 2018

(51) Int. Cl.
*A61G 9/00* (2006.01)
*A47K 10/48* (2006.01)
(Continued)

(52) U.S. Cl.
CPC .............. *A61G 9/006* (2013.01); *A47K 10/48* (2013.01); *A61F 5/453* (2013.01); *A61G 9/00* (2013.01); *A61G 9/02* (2013.01); *B05B 3/02* (2013.01)

(58) Field of Classification Search
CPC .......... A61F 5/451; A61F 5/453; A61F 5/455; A61G 9/00; A61G 9/006
See application file for complete search history.

(56) References Cited

U.S. PATENT DOCUMENTS

| 6,248,096 B1 * | 6/2001 | Dwork | A61F 5/453 |
| | | | 604/347 |
| 7,387,619 B2 * | 6/2008 | Kitamura | A61F 5/451 |
| | | | 324/686 |
| 2007/0032765 A1 * | 2/2007 | Honda | A61F 5/451 |
| | | | 604/347 |

FOREIGN PATENT DOCUMENTS

| JP | 2003153931 A | 5/2003 |
| KR | 100422921 B1 | 3/2004 |

(Continued)

OTHER PUBLICATIONS

Int'l Search Report dated Sep. 21, 2015 in Int'l Application No. PCT/KR2015/001117.

*Primary Examiner* — Janie M Loeppke
(74) *Attorney, Agent, or Firm* — Panitch Schwarze Belisario & Nadel LLP (57) ABSTRACT

An excreta disposal apparatus includes a body comprising a seating unit correspondingly shaped to the curved shape of the genital area and buttocks of a human body, a urine disposal unit corresponding to the genital area, an excrement disposal unit corresponding to the buttocks, and a disposal space open toward the genital area and buttocks to receive excreta discharged from the human body. A main body unit, for mounting between the legs of the human body, is connected to the seating unit and has an accommodation space therein. A discharge channel is provided in the accommodation space and communicates with the disposal space to discharge the excreta in the disposal space to the outside. The body also includes a genital insertion unit, which has the urine disposal unit therein, formed to surround the circumference of at least a part of male genitalia.

7 Claims, 12 Drawing Sheets

(51) Int. Cl.
  *A61F 5/453*   (2006.01)
  *A61G 9/02*    (2006.01)
  *B05B 3/02*    (2006.01)

(56) References Cited

FOREIGN PATENT DOCUMENTS

| KR | 200453814 Y1 | 5/2011 |
| KR | 20120097946 A | 9/2012 |
| KR | 20130055594 A | 5/2013 |

\* cited by examiner

EXCRETA DISPOSAL APPARATUS COMPRISING MALE MODULE

CROSS-REFERENCE TO RELATED APPLICATION

This application is a Section 371 of International Application No. PCT/KR2015/001117, filed Feb. 3, 2015, which was published in the Korean language on Aug. 11, 2016, under International Publication No. WO 2016/125928 A1, the disclosure of which is incorporated herein by reference.

TECHNICAL FIELD

The present invention relates to an excreta disposal apparatus for automatically disposing an excreta discharged from a human body, and more particularly, to an excreta disposal apparatus comprising a male module corresponding to a male body shape.

BACKGROUND ART

In general, since the patients or the elderly, who have mobility difficulties or who are unable to move their lower body by their own will, do not have the ability to handle their own excreta, there is an inconvenience that a guardian or a caregiver should always reside at hand.

Therefore, in order to solve such an inconvenience, an excreta disposal apparatus for collecting excreta by directly contacting the body has been researched and developed. Such an excreta disposal apparatus is designed to receive and suck a user's excreta and discharge the excreta to the outside so that the excreta can be automatically treated even if the guardian or the caregiver does not reside around the user.

However, since the disposal apparatus is designed without considering the body of the user and is concentrated only on the function of the excreta disposal, the conventional excreta disposal apparatus developed to date has a problem that the usability is very low. Generally, since a part around the buttocks or the genital area where excreta is excreted is sharply curved and the excreta disposal apparatus is difficult to adhered, there are many cases where the excreta leaks out between the human body and the excreta disposal apparatus.

In addition, the users, such as the patients or the elderly, who use the excreta disposal apparatus often live in a bed and frequently cannot change their posture on their own. When such a state persists for a long time, a bedsore occurs, so that it is necessary to periodically change the posture. However, since the posture cannot be changed in the state where the excreta disposal apparatus is worn, there is an inconvenience to remove the excreta disposal apparatus.

In addition, since the shape of the body is formed very differently according to gender, it is necessary to change the structure according to each gender. However, conventionally, there is an inconvenience in that the excreta disposal apparatus specialized for each gender has not been researched and developed.

Therefore, a method for solving such problems is required.

DISCLOSURE

Technical Problem

The present invention has been made in view of the above problems, and provides an excreta disposal apparatus capable of preventing leakage of excreta while a user wears the excreta disposal apparatus, and improving the feelings of wearing.

The present invention further provides an excreta disposal apparatus which can be free from the limitation of the behavior even when the user wears the excreta disposal apparatus.

The present invention further provides an excreta disposal apparatus which can provide a specialized structure according to a male body shape.

The problems of the present invention are not limited to the above-mentioned problems, and other problems not mentioned can be clearly understood by those skilled in the art from the following description.

Technical Solution

In an aspect, there is provided an excreta disposal apparatus comprising a male module, the apparatus including: a body including a seating unit, which has a shape corresponding to a curved shape of genital area and buttocks of a human body, comprises a urine disposal unit corresponding to the genital area of the human body and an excrement disposal unit corresponding to the buttocks of the human body, and has a disposal space open toward the genital area and buttocks of the human body so as to take excreta discharged from the human body, and a main body unit, which is connected to the seating unit so as to be mounted between legs of the human body and has an accommodation space therein; and a discharge channel, which is provided in the accommodation space and communicates with the disposal space so as to discharge the excreta in the disposal space to the outside, wherein the body comprises a genital insertion unit, which has the urine disposal unit therein and is formed so as to surround a circumference of at least a part of male genitalia.

The urine disposal unit is partitioned by the excrement disposal unit.

The male module is detachable.

The male module includes a connection unit configured to connect the genital insertion unit to the body.

The apparatus further includes a spray unit which is exposed to the disposal space and sprays washing water.

The apparatus further comprising a flow channel switching unit which is provided in the accommodation space and supplies the washing water introduced from the outside to the spray unit.

The spray unit includes: an upper side nozzle which is provided in the genital insertion unit, and sprays the washing water to the urine disposal unit; an auxiliary nozzle which is provided in the connection unit, and sprays the washing water to the excrement disposal unit; and a rotary nozzle which is exposed to the excrement disposal unit, and sprays the washing water to the excrement disposal unit.

The apparatus further includes: a first supply channel which flows the washing water accommodated in the flow channel switching unit to the rotary nozzle; and a second supply channel which flows the washing water accommodated in the flow channel switching unit to the male module.

The apparatus further includes: a first branch flow path which is connected to the second supply channel, and provided in the connection unit to flow the washing water to the auxiliary nozzle; and a second branch flow path which is connected to the second supply channel, and provided in the genital insertion unit to flow the washing water to the upper side nozzle.

The apparatus further includes: a urine discharge flow path which is provided in the genital insertion unit and flows a urine accommodated in the urine disposal unit to the outside of the genital insertion unit; and an auxiliary discharge channel which is connected to the urine discharge flow path and flows the urine to the discharge channel.

The genital insertion unit is formed to be adjustable in length.

Advantageous Effects

In order to solve the above-described problems, the present invention provides an excreta disposal apparatus comprising a male module having the following effects.

First, since the seating unit is formed to correspond to the curved shape of the genital area and buttocks of a user and can be adhered to the user's body, there is an advantage that the leakage of the excreta can be prevented in a state where the user wears the excreta disposal apparatus.

Secondly, since the main body unit also has a size corresponding to the width between the legs of the user, there is an advantage that the posture of the user can be maintained naturally.

Third, there is an advantage that the user's feelings of wearing is greatly improved.

Fourth, there is an advantage that the user is not restricted in the behavior even when the user wears the excreta disposal apparatus, and the posture can be freely changed.

Fifth, since a male module having a structure specialized for a male body shape is provided, there is an advantage that the excreta can be smoothly handled by stably fixing the male genitalia having a high degree of freedom of the genitalia.

The effects of the present invention are not limited to the effects mentioned above, and other effects not mentioned can be clearly understood by those skilled in the art from the description of the claims.

MODE FOR INVENTION

Hereinafter, preferred embodiments of the present invention will be described with reference to the accompanying drawings. In describing the present embodiment, the same designations and the same reference numerals are used for the same components, and further description thereof will be omitted.

Figure 1:
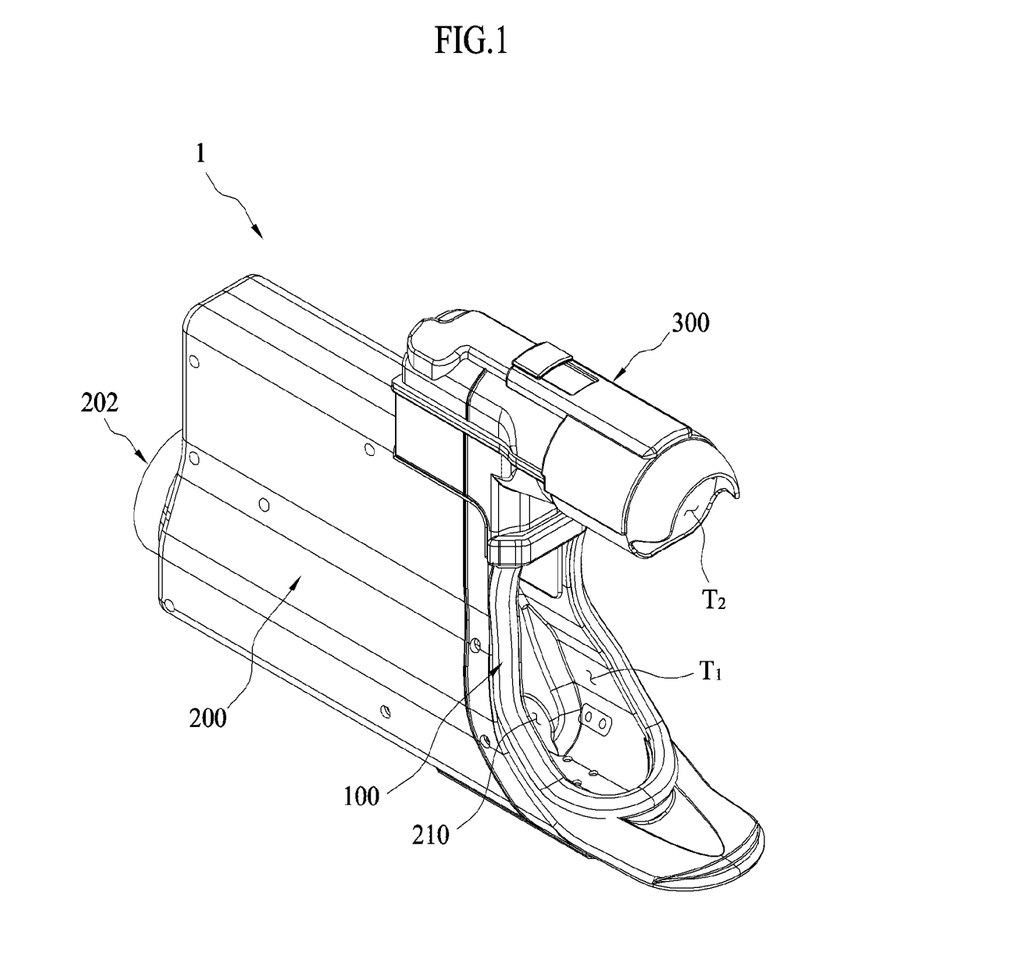
FIG. 1 is a perspective view showing an entire structure of an excreta disposal apparatus according to an embodiment of the present invention.

FIG. 1 is a perspective view showing an entire structure of an excreta disposal apparatus 1 according to an embodiment of the present invention.

As shown in FIG. 1, the excreta disposal apparatus 1 according to an embodiment of the present invention includes a body including a seating portion 100 and a main body unit 200, and a discharge channel 210. In addition, the body may include a male module 300.

The seating portion 100 has a curved shape corresponding to a curvature of the genital area and buttocks of a human body, and has disposal spaces T1 and T2 which are opened in the direction of the genital area and buttocks and receive the excreta discharged from the human body.

Here, the genital area of the human body refers to an area around the genitalia of male and female, and the buttocks are connected to the above-mentioned genital area and refers to an area around the anus. That is, the seating portion 100 is formed to be seated in the groin of the human body, and has a curved shape corresponding to the curvature.

The disposal spaces T1 and T2 are formed to have a certain volume so as to receive excreta including urine and excrement. The disposal spaces T1 and T2 of the present embodiment include a urine disposal unit T2 corresponding to the genital area of the human body and an excrement disposal unit T1 corresponding to the buttocks of the human body.

That is, in the case of the present embodiment, the disposal spaces T1 and T2 are partitioned by a male module 300 so as to separately dispose of urine and excrement. However, unlike the present embodiment, it is obvious that the urine disposal unit and the excrement disposal unit may be connected without being partitioned.

The main body unit 200 is connected to the seating portion 100 so as to be mounted between the legs of the human body when a user wears the excreta disposal apparatus 1. That is, the user can stretch his/her legs to both sides of the main body unit 200 in a state in which the seating portion 100 is in close contact with the genital area and buttocks, so that the user can wear the excreta disposal apparatus 1 stably.

In addition, although not shown in the drawing, an accommodation space is provided inside the main body unit 200, and various elements may be provided in the accommodation space. This will be described later.

Meanwhile, for convenience of explanation, the open direction side of the disposal spaces T1 and T2 is defined as a front side, and the opposite direction is defined as a rear side. Further, the direction in which the urine disposal unit T2 is provided is defined as an upper side and the opposite direction is defined as a lower side.

The discharge channel 210 is provided in the accommodation space and communicates with the disposal spaces T1 and T2 to discharge the excreta of the disposal spaces T1 and T2 to the outside. Particularly, in the present embodiment, a through hole 202 is formed in the rear side of the main body unit 200 so that an external connection pipe can be inserted into the accommodation space.

The connection pipe may include an excreta flow pipe connected to suck excreta by using a separate suction device, a washing water feeding pipe for supplying washing water, and the like. That is, the discharge channel 210 is connected to the excreta flow pipe so that the excreta can be discharged to the outside.

Figure 2:
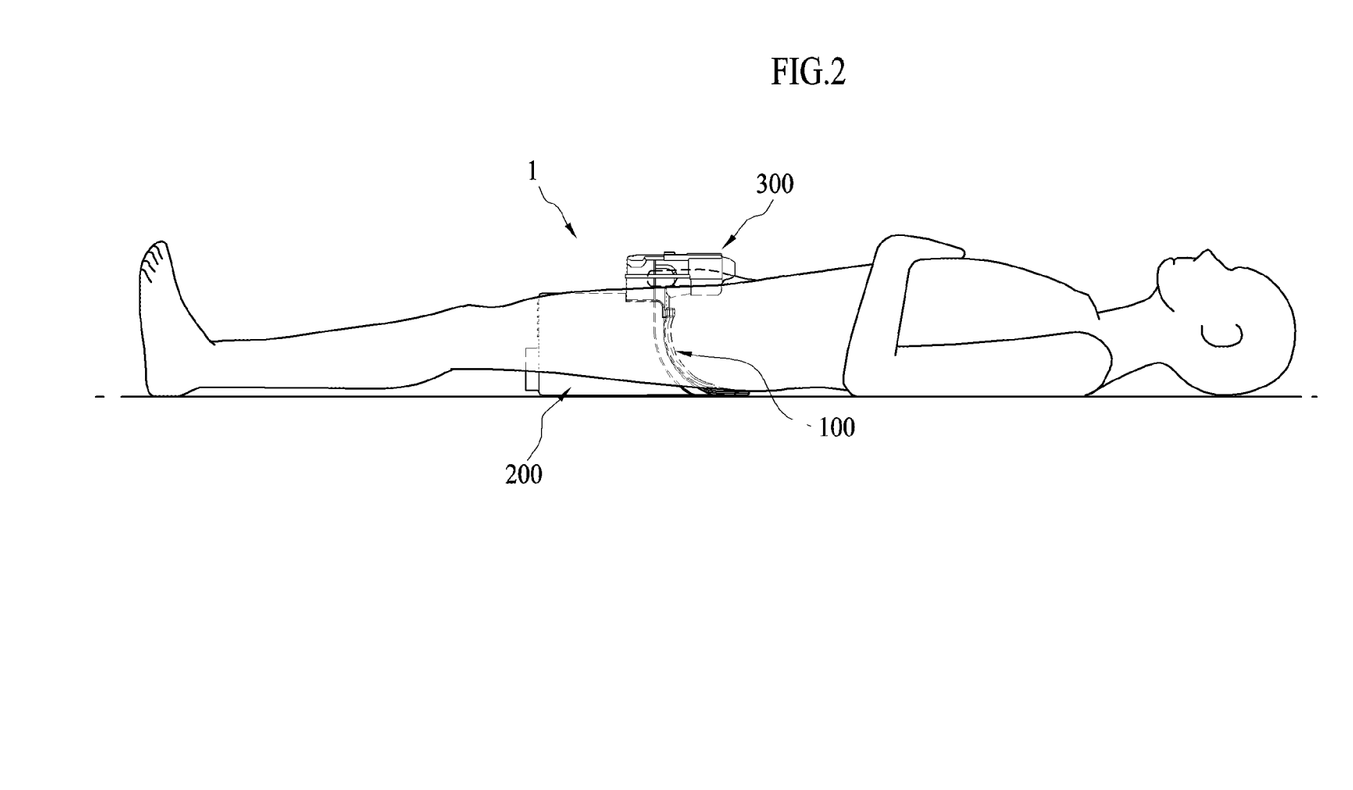
FIG. 2 is a side view of an excreta disposal apparatus worn on a human body according to an embodiment of the present invention.

FIG. 2 is a side view of an excreta disposal apparatus 1 worn on a human body according to an embodiment of the present invention.

As shown in FIG. 2, the user adheres the seating portion 100 to the genital area and buttocks while lying on a bed or the like, and stretches legs on both sides of the main body unit 200 to stably wear the excreta disposal apparatus. As described above, since the excreta disposal apparatus 1 according to an embodiment of the present invention is formed to correspond to the shape of the human body, there is no need for the user to change the posture forcibly according to the excreta disposal apparatus 1, and a natural posture can be maintained.

In addition, even if the user changes his/her posture from side to side or the like, it can be moved along the user's body without being detached, and does not interfere with user's movement in a state of being positioned between the user's legs even when the user moves.

Figure 3:
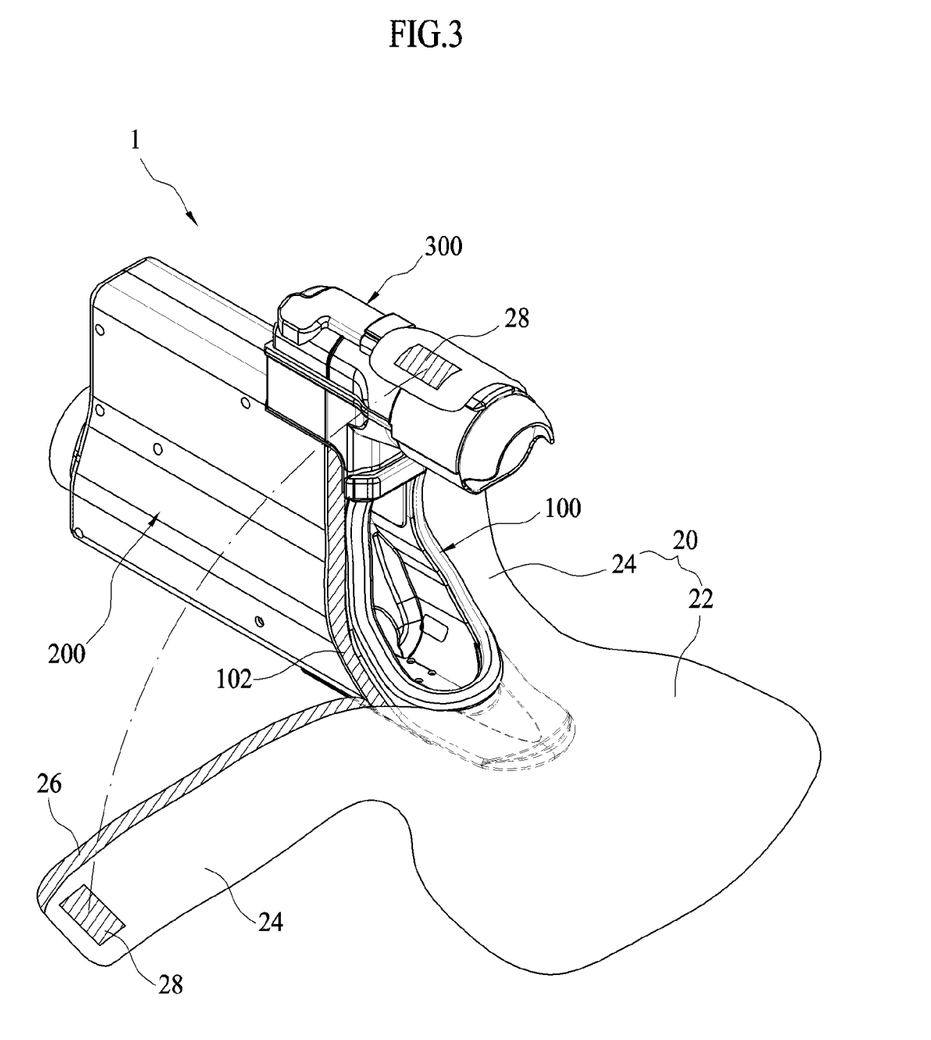
FIG. 3 is a perspective view showing a state where a pad is attached to a seating unit of an excreta disposal apparatus according to an embodiment of the present invention.

FIG. 3 is a perspective view showing a state where a pad 20 is attached to the seating portion 100 of the excreta disposal apparatus 1 according to an embodiment of the present invention.

As shown in FIG. 3, the excreta disposal apparatus 1 according to an embodiment of the present invention may include a pad 20 detachably installed to surround the seating portion 100. The pad 20 may be made of fabric or the like to improve the wearer's feeling of wearing, and may stably fix the excreta disposal apparatus 1 to the user's body.

In the case of the present embodiment, the pad 20 includes a pack portion 22 and a wing portion 24. The pack portion 22 is attached to the lower side of the seating portion 100 so as to surround the circumference of the user's buttocks. The wing portion 24 is attached so as to surround the circumference of the seating portion 100. Meanwhile, in order to attach the pad 20 to the seating portion 100, the seating portion 100 and the pad 20 may be provided with a Velcro. That is, a seating unit Velcro 102 and a pad Velcro 26 are formed to correspond to each other, so that the pad 20 can be easily attached. In addition, in the present embodiment, each wing portion 24 is provided with a fixation Velcro 28 so that respective wing portions 24 can be fixed to each other.

Figure 4:
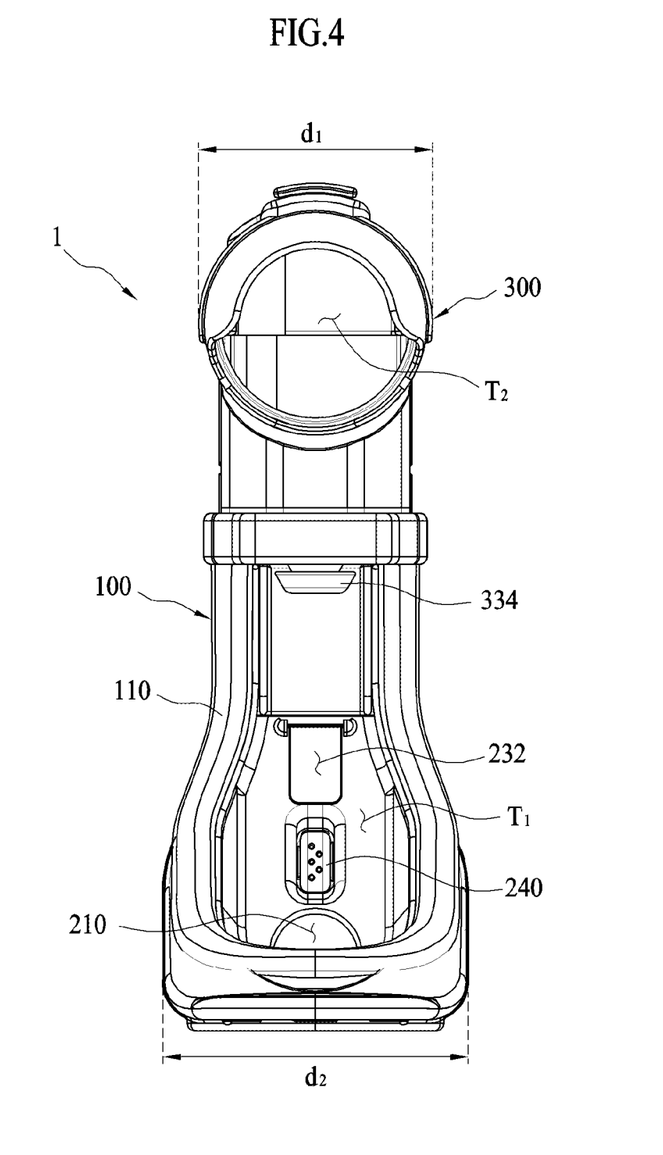
FIG. 4 is a front view of an excreta disposal apparatus according to an embodiment of the present invention.

FIG. 4 is a front view of the excreta disposal apparatus 1 according to an embodiment of the present invention.

FIG. 4 shows the disposal spaces T1 and T2 of the seating portion 100 in more detail. As described above, in the present embodiment, the disposal spaces T1 and T2 include the urine disposal unit T2 and the excrement disposal unit T1. Various elements for disposing of the excreta may be provided in the disposal spaces T1 and T2.

A spray unit is an element that is exposed to the disposal spaces T1 and T2 to spray washing water, and may include one or more spraying nozzles. In the case of the present embodiment, the spray unit is provided with a rotary nozzle 240 for spraying washing water to the excrement disposal unit T1 side, an auxiliary nozzle 334, and, although not shown, an upper side nozzle for spraying washing water to the urine disposal unit T2 side.

That is, the angle of the rotary nozzle 240 can be controlled to wash the periphery of the buttocks of the human body, and the auxiliary nozzle 334 sprays washing water so as to wash the surface of the excrement disposal unit T1. In addition, the upper side nozzle also sprays washing water to wash the genital area and the surface of the urine disposal unit T2.

In addition, in the present embodiment, a drying air jet opening 232 is formed in the disposal space T1 and T2 to allow a drying air to flow and be jetted, thereby rapidly drying the water after washing.

Meanwhile, as shown in the drawing, the body including the seating portion 100 and the main body unit is formed in such a manner that a width d1 of the upper portion is narrower than a width d2 of the lower portion when viewed from the front. That is, it has a shape corresponding to the curved shape of a thigh portion of the human body, so that both legs of the user can be stably adhered to both sides of the body of the excreta disposal apparatus 1. In addition, the body is formed to have a width corresponding to the width between the legs of the user, so that the user can take a natural posture without opening his/her legs forcibly.

In the present embodiment, a fastening member 110 is provided around the seating portion 100 to be in close contact with the user's body. The fastening member 110 is provided in a band shape along the circumferential line of the seating portion 100, so that the feelings of wearing can be improved.

Figure 5:
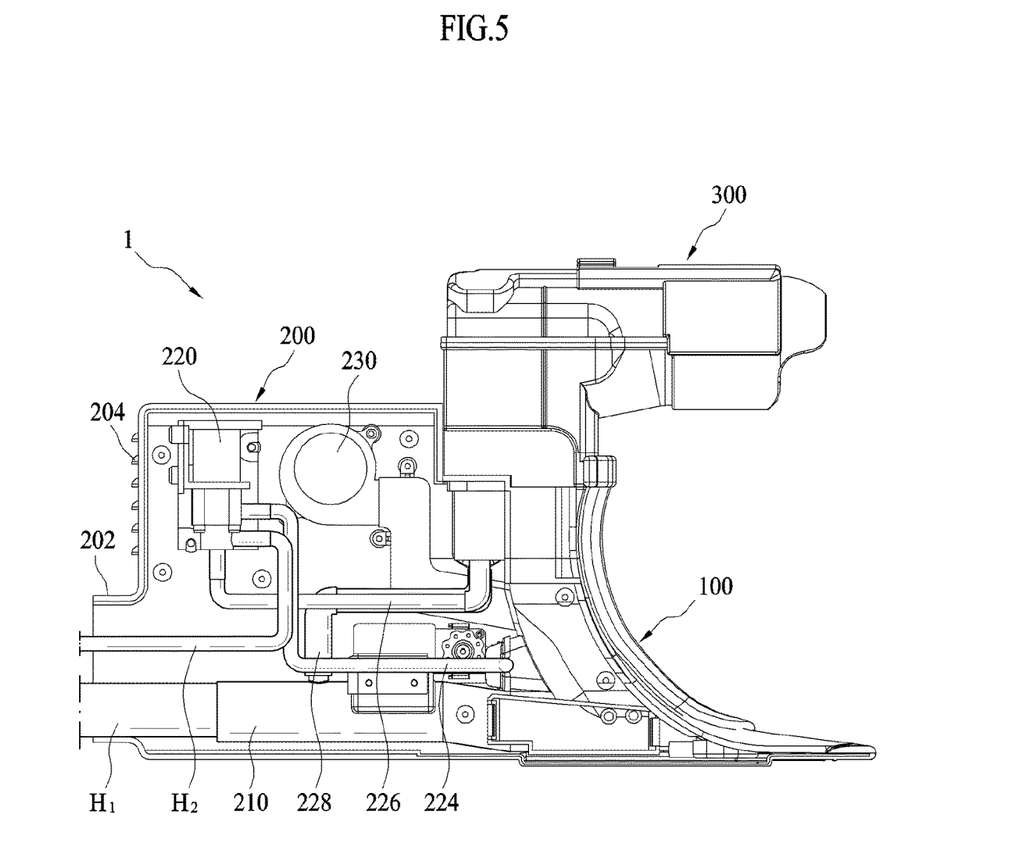
FIG. 5 is a cross-sectional view showing an internal structure of a main body unit in an excreta disposal apparatus according to an embodiment of the present invention.

FIG. 5 is a cross-sectional view showing an internal structure of the main body unit 200 in the excreta disposal apparatus 1 according to an embodiment of the present invention.

As shown in FIG. 5, an accommodation space is formed inside the main body unit 200, and the accommodation space may be provided with various elements. In the present embodiment, the accommodation space is provided with the above mentioned discharge channel 210, a flow channel switching unit 220, and an air blowing unit 230.

The discharge channel 210 is connected to an excreta flow tube H1 that is introduced through the through hole 202 to discharge the excreta to the outside. Particularly, in the present embodiment, the urine received from the male module 300 side can be introduced into the discharge channel 210 through an auxiliary discharge channel 228.

The flow channel switching unit 220 is an element which is connected to a washing water feeding pipe H2 introduced through the through hole 202 and receives the washing water from the outside, and ramifies and supplies the washing water to a plurality of spray nozzles through a solenoid valve or the like. Specifically, in the present embodiment, the washing water stored in the flow channel switching unit 220 may flow to the rotary nozzle through a first supply channel 224 and may flow to the auxiliary nozzle and the upper side nozzle through a second supply channel 226.

The air blowing unit 230 is an element which blows dry air to the disposal space, can generate dry air by using a blowing fan or the like, and can blow the dry air to the disposal space side through the drying air jet opening. Further, a heater may be further provided so as to increase the temperature of the dry air.

In the present embodiment, an air inlet 204 is formed on the rear surface of the main body unit 200 to allow an external air to flow to ventilate the inside of the accommodation space.

Hereinafter, the male module 300 provided in the present embodiment will be described in more detail.

Figure 6:
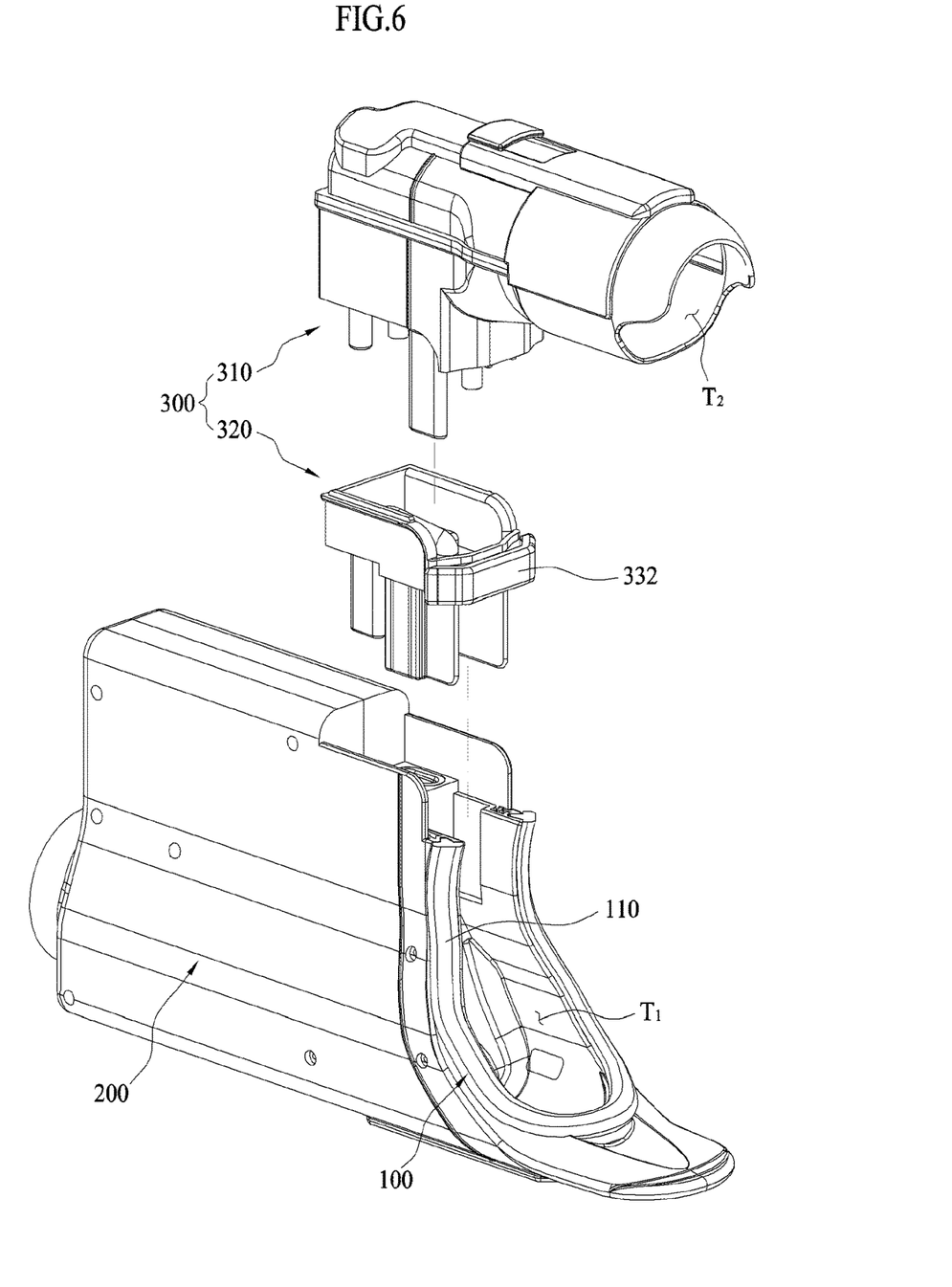
FIG. 6 is a perspective view showing a decomposition structure of a male module in an excreta disposal apparatus according to an embodiment of the present invention.

FIG. 6 is a perspective view showing a decomposition structure of the male module 300 in the excreta disposal apparatus according to an embodiment of the present invention.

As shown in FIG. 6, in the present embodiment, the male module 300 may include a genital insertion unit 310 which has a urine disposal unit T2 formed therein and is configured to surround the circumference of a male genitalia, and a connection unit 320 configured to connect the genital insertion unit 310 to the body. In the present embodiment, the male module 300 is detachably formed, but is not limited thereto and may be formed integrally with the body.

That is, the genital insertion unit 310 has a shape corresponding to the shape of male genitalia, and is formed to receive urine in a state where at least a part of male genitalia is inserted.

Accordingly, the male genitalia having a high degree of freedom of movement can be stably fixed, so that the urine can be prevented from being indiscriminately discharged according to the direction of the male genitalia and only a minimum range can be contaminated.

In the present embodiment, the urine disposal unit T2 is configured to be separated from the excrement disposal unit T1 by the male module 300, and the urine may be introduced into the discharge channel through the above mentioned auxiliary discharge channel. That is, it is possible to prevent the urine from entering the excrement disposal unit T1 and contaminating the user's buttocks.

As described above, in the present embodiment, the urine disposal unit T2 of the male module 300 is configured to be partitioned from the above mentioned excrement disposal unit T1, but the present invention is not limited thereto. That is, unlike the present embodiment, the urine disposal unit T2 may communicate with the excrement disposal unit T1, and in this case, the auxiliary discharge channel may not be separately provided.

Figure 7:
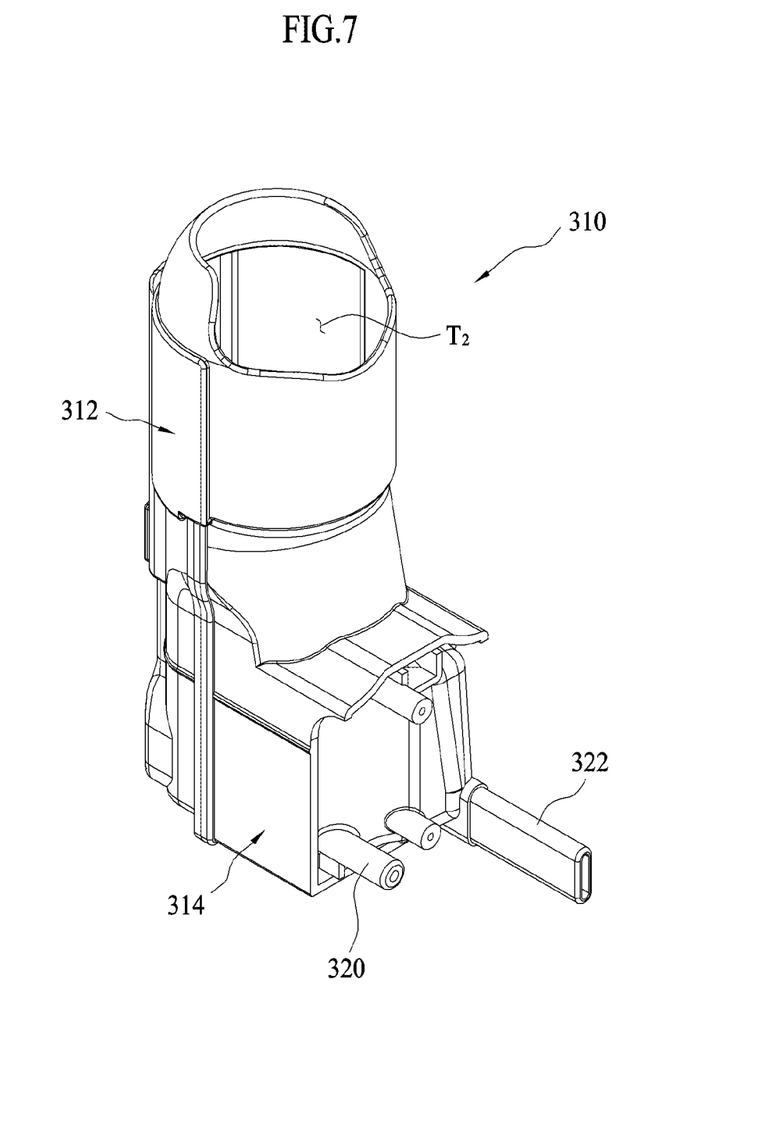
FIG. 7 is a perspective view showing a state of a genital insertion unit in an excreta disposal apparatus according to an embodiment of the present invention.

FIG. 7 is a perspective view showing a state of a genital insertion unit 310 in an excreta disposal apparatus according to an embodiment of the present invention.

As shown in FIG. 7, the genital insertion unit 310 of the present embodiment includes a connection portion 314 connected to the connection unit and an insertion portion 312 into which a male genitalia is inserted. The genital insertion unit 310 is provided with a second branch flow path 330 which is branched from the above mentioned second supply channel and flows the washing water to the upper side nozzle and a urine discharge flow path 322 which flows the urine accommodated in the urine disposal unit T2 to the above mentioned auxiliary discharge channel.

That is, the genital insertion unit 310 is provided with a path through which the washing water is introduced and a path through which the urine is discharged.

Figure 8:
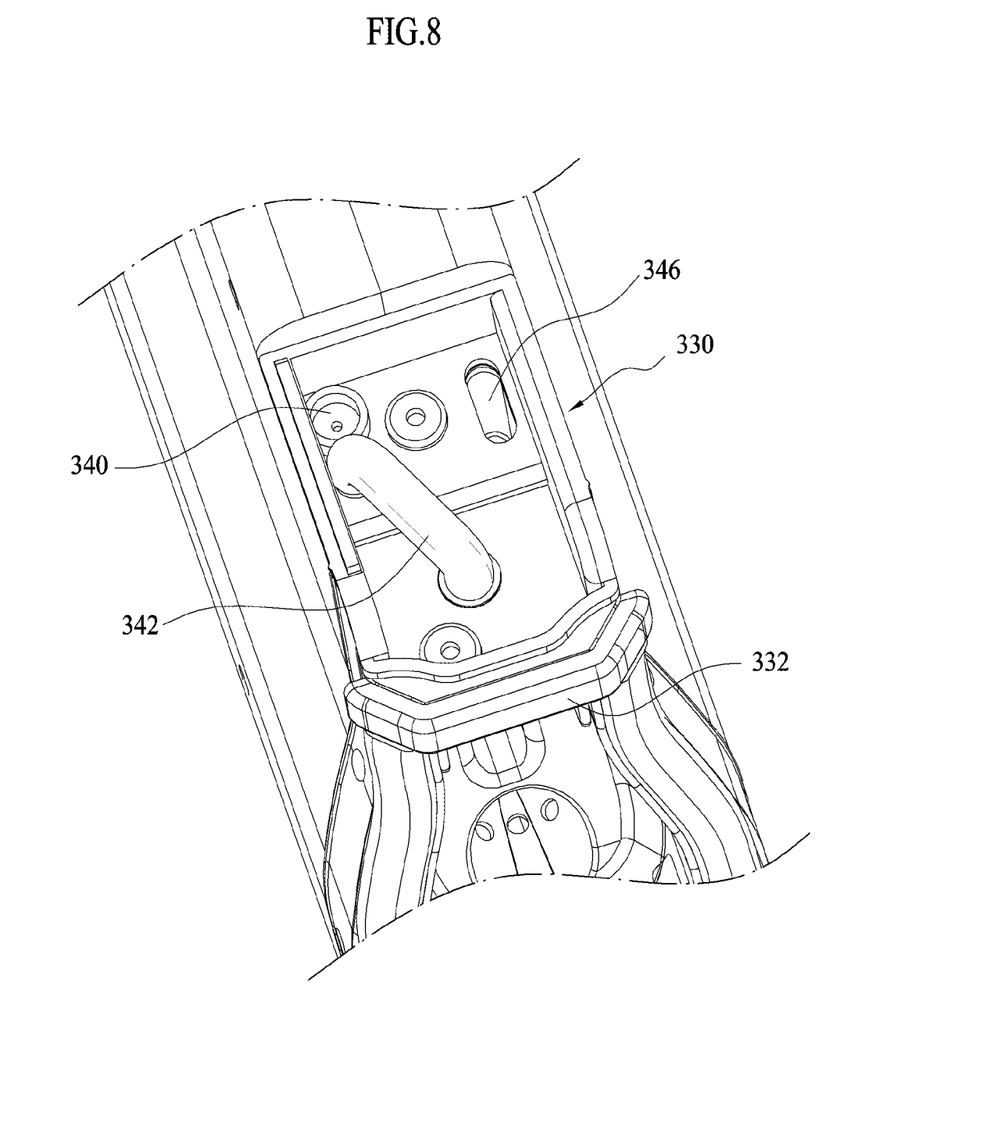
FIG. 8 is a perspective view of a connection unit in an excreta disposal apparatus according to an embodiment of the present invention.

FIG. 8 is a perspective view of the connection unit 320 in an excreta disposal apparatus according to an embodiment of the present invention.

As shown in FIG. 8, the connection unit 320 of the present embodiment is formed with a coupling hole into which the genital insertion unit can be coupled and, in particular, formed with a first coupling hole 340 into which the second branch flow path is inserted and a second coupling hole 346 into which the urine discharge flow path is inserted. That is, the second branch flow path is inserted into the first coupling hole 340 and connected to the second supply channel, and the urine discharge flow path may be inserted into the second coupling hole 346 and connected to the auxiliary discharge channel.

Meanwhile, the connection unit 320 is provided with a first branch flow path 342 which is branched from the above mentioned second supply channel and flows the washing water to the auxiliary nozzle. That is, the washing water flowing into the second supply channel may be branched in both directions of the first branch flow path 342 and the second branch flow path.

Figure 9:
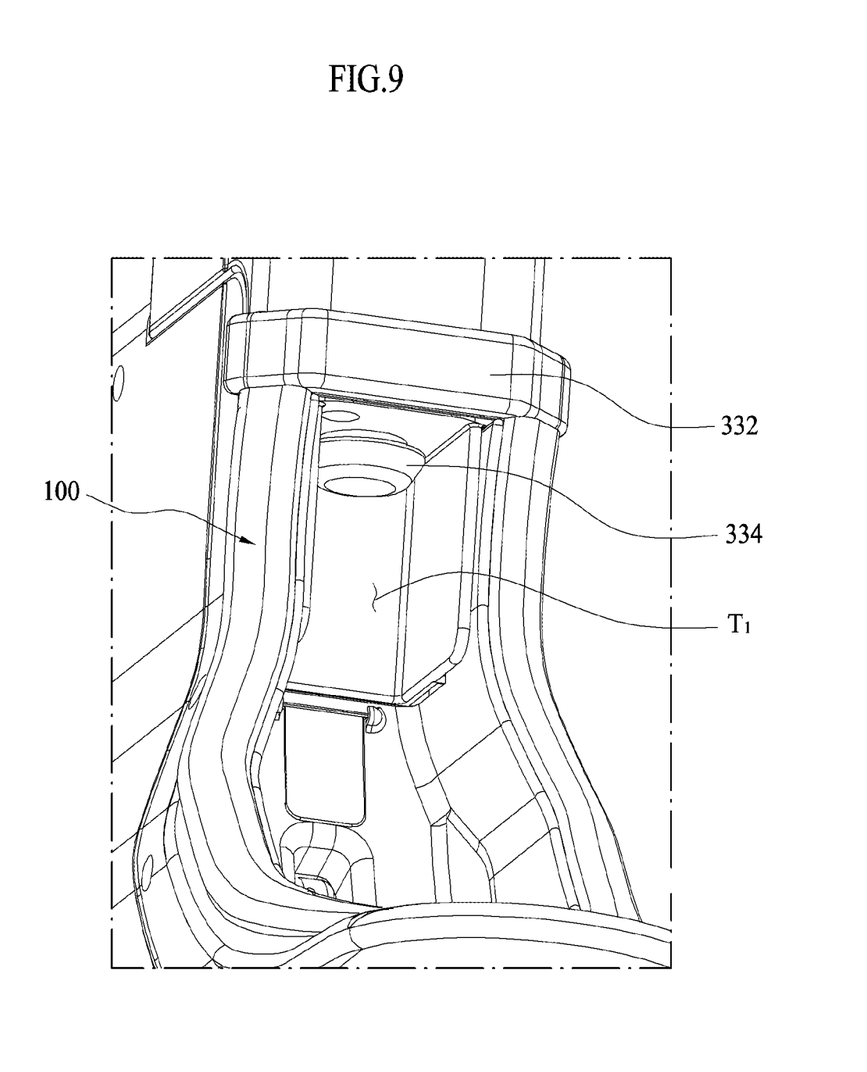
FIG. 9 is a perspective view of an auxiliary nozzle provided in a male module in an excreta disposal apparatus according to an embodiment of the present invention.

FIG. 9 is a perspective view of the auxiliary nozzle 334 provided in a male module in an excreta disposal apparatus according to an embodiment of the present invention.

As shown in FIG. 9, the male module may be provided with the auxiliary nozzle 334 which is exposed to the excrement disposal unit T1 side and sprays the washing water. Since the auxiliary nozzle 334 is provided in the upper side of the excrement disposal unit T1, the entire surface of the excrement disposal unit T1 can be washed thoroughly.

At this time, the washing water supplied to the auxiliary nozzle 334 may flow into the male module from the above described second supply channel, may be branched through the first branch flow path, and may be transmitted to the auxiliary nozzle 334 side.

Meanwhile, an auxiliary fastening member 332 connected to the fastening member of the body side may be provided in the lower side of the male module. The auxiliary fastening member 332 is provided to be in contact with the fastening member of the body side in a state where the male module is coupled to the body, so that the excrement disposal unit T1 can be sealed.

Figure 10:
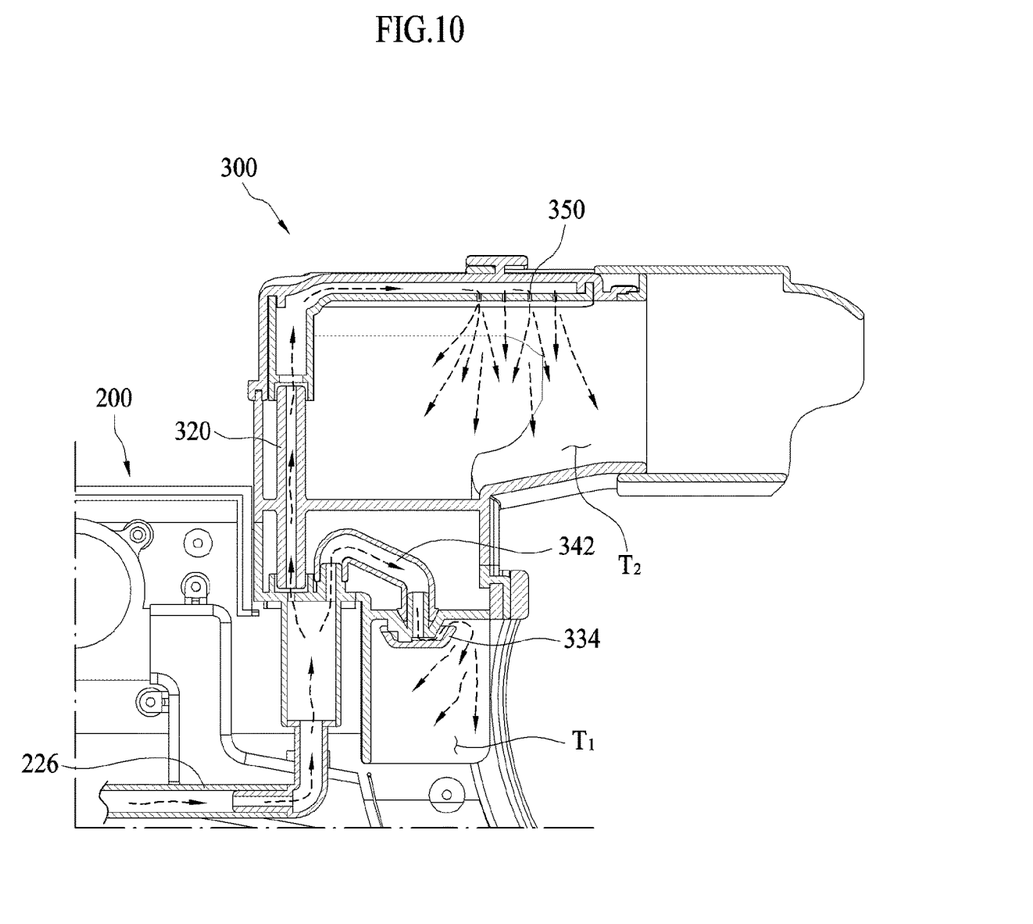
FIG. 10 is a cross-sectional view showing a branch structure of washing water in an excreta disposal apparatus according to another embodiment of the present invention.

FIG. 10 is a cross-sectional view showing a branch structure of washing water in an excreta disposal apparatus according to another embodiment of the present invention.

Referring to FIG. 10, the branch structure of the above described washing water can be more easily checked. As shown in the drawing, the washing water flowing into the male module 300 through the second supply channel 226 is branched into the first branch flow path 342 and the second branch flow path 330, and these branched washing water may be sprayed to an upper side nozzle 350 and the auxiliary nozzle 334 respectively.

That is, according to an embodiment of the present invention, the male module 300 partitions the urine disposal unit T2 and the excrement disposal unit T1, so that the urine and the excrement are not mixed with each other and the washing water may be sprayed to both disposal unit sides, thereby maintaining the cleanliness of the disposal space.

Figure 11:
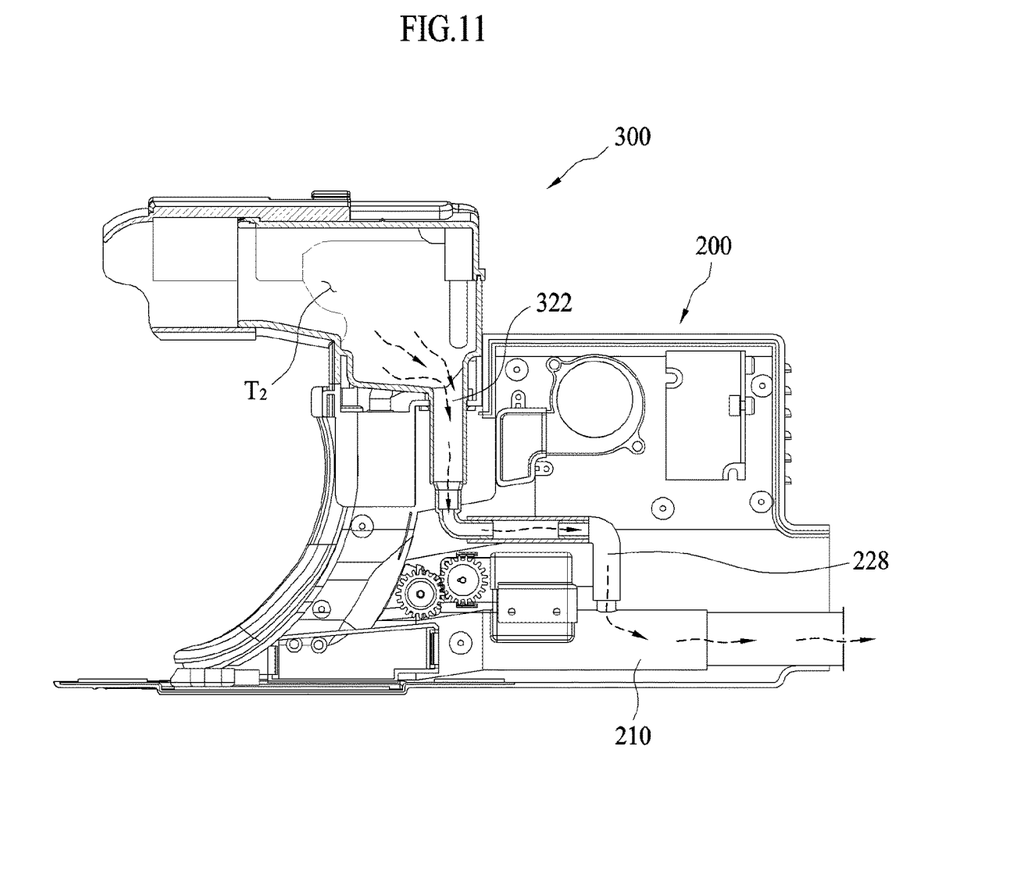
FIG. 11 is a cross-sectional view showing a urine discharge structure in an excreta disposal apparatus according to another embodiment of the present invention.

FIG. 11 is a cross-sectional view showing a urine discharge structure in an excreta disposal apparatus according to another embodiment of the present invention.

Referring to FIG. 11, the above mentioned urine discharge structure can be more easily checked. As shown in the drawing, the urine accommodated in the urine disposal unit T2 of the male module 300 may be transferred to the auxiliary discharge channel 228 through the urine discharge flow path 322, and then the auxiliary discharge channel 228 may transfer the urine to the discharge channel 210.

That is, according to an embodiment of the present invention, since the male module 300 partitions the urine disposal unit T2 and the excrement disposal unit T1, the urine and the excrement are not mixed with each other and the urine and the excrement can be collected in the inside of the main body unit and be discharged to the outside with only a single flow path.

Figure 12:
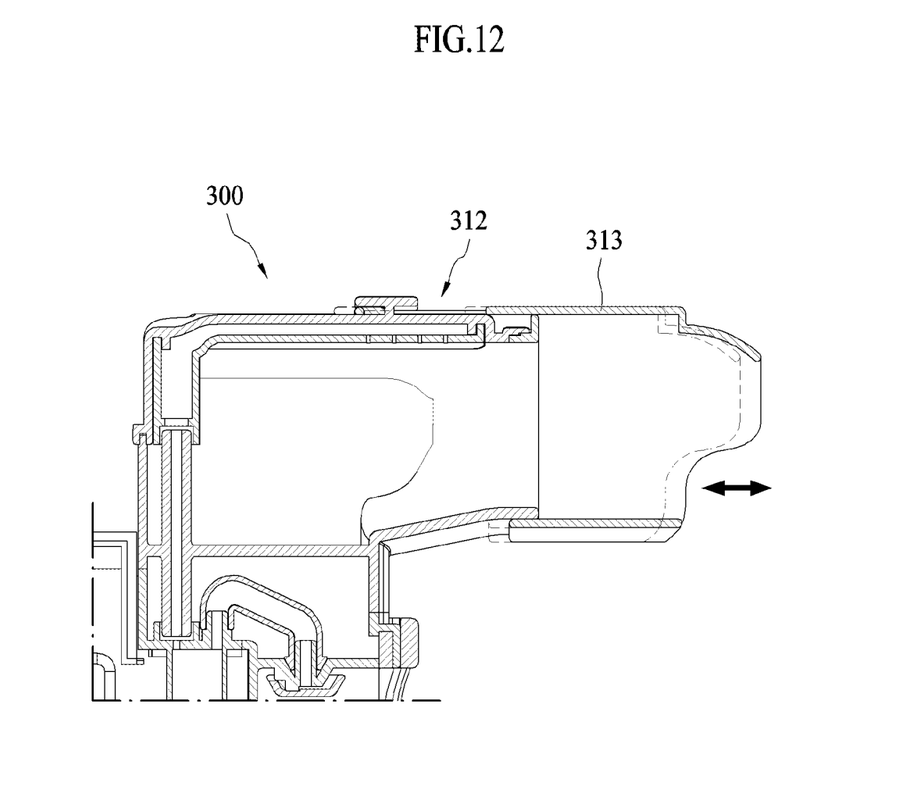
FIG. 12 is a cross-sectional view showing a state in which a length of a genital insertion unit is varied in an excreta disposal apparatus according to another embodiment of the present invention.

FIG. 12 is a cross-sectional view showing a state in which a length of a genital insertion unit is varied in an excreta disposal apparatus according to another embodiment of the present invention.

As shown in FIG. 12, the genital insertion unit of the male module 300 of the excreta disposal apparatus according to the present embodiment can be formed to be adjustable in length. In particular, in the present embodiment, a sliding member 313 is provided in the front side of the insertion portion 312, and the sliding member 313 can adjust the length of the genital insertion unit according to the back and forth movement.

Accordingly, the excreta disposal apparatus of the present embodiment can be adapted to the shape of various genitalia, and can be applied to unspecified individuals.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims. Accordingly, the scope of the present invention is not construed as being limited to the described embodiments but is defined by the appended claims as well as equivalents thereto.

The invention claimed is:

1. An excreta disposal apparatus comprising a male module, the apparatus comprising:
   a body comprising a seating unit, which has a shape corresponding to a curved shape of genital area and buttocks of a human body, comprises a urine disposal unit corresponding to the genital area of the human body and an excrement disposal unit corresponding to the buttocks of the human body, and has a disposal space open toward the genital area and buttocks of the human body so as to take excreta discharged from the human body, and a main body unit, which is connected to the seating unit so as to be mounted between legs of the human body and has an accommodation space therein;
   a discharge channel, which is provided in the accommodation space and communicates with the disposal space so as to discharge the excreta in the disposal space to outside of the excreta disposal apparatus;
   a spray unit, which is exposed to the disposal space and sprays washing water; and
   a flow channel switching unit, which is provided in the accommodation space and supplies the washing water introduced from outside of the excreta disposal apparatus to the spray unit, wherein the body comprises:
   a genital insertion unit, which has the urine disposal unit therein and is formed so as to surround a circumference of at least a part of male genitalia;
   a urine discharge flow path, which is provided in the genital insertion unit and to enable urine to flow to the main body part from the genital insertion unit, and which is formed in a protruding fashion;
   a second branch flow path, which is provided in the genital insertion unit to enable to flow washing water accommodated from the main body part to the genital insertion unit and is formed in a protruding fashion;
   a first coupling hole, which is formed in a groove shape corresponding to the second branch flow path, and which interconnects the second branch flow path with the main body part while fixing the genital insertion unit to the main body part when the second branch flow path is inserted and coupled; and
   a second coupling hole, which is formed in a groove shape corresponding to the urine discharge flow path, and which interconnects the urine discharge flow path with the main body part while fixing the genital insertion unit to the main body part when the urine discharge flow path is inserted and coupled.

2. The apparatus of claim 1, wherein the urine disposal unit is partitioned by the excrement disposal unit.

3. The apparatus of claim 1, wherein the spray unit comprises:
   an upper side nozzle which is provided in the genital insertion unit, and sprays the washing water to the urine disposal unit;
   an auxiliary nozzle which is provided in the connection unit, and sprays the washing water to the excrement disposal unit; and
   a rotary nozzle which is exposed to the excrement disposal unit, and sprays the washing water to the excrement disposal unit.

4. The apparatus of claim 3, further comprising:
   a first supply channel, through which flows the washing water accommodated in the flow channel switching unit to the rotary nozzle; and
   a second supply channel, through which flows the washing water accommodated in the flow channel switching unit to the male module.

5. The apparatus of claim 4, further comprising:
   a first branch flow path which is connected to the second supply channel, and provided in the connection unit to enable the washing water to flow to the auxiliary nozzle.

6. The apparatus of claim 1, further comprising:
   an auxiliary discharge channel which is connected to the urine discharge flow path and allows the urine to flow to the discharge channel.

7. The apparatus of claim 1, wherein the genital insertion unit is formed to be adjustable in length.

* * * * *